United States Patent [19]
La Rocca

[11] Patent Number: 4,865,545
[45] Date of Patent: Sep. 12, 1989

[54] DENTAL ASPIRATOR

[76] Inventor: Nina La Rocca, 13873 Trenton Trail, Middleburg Heights, Ohio 44130

[21] Appl. No.: 224,905

[22] Filed: Jul. 27, 1988

[51] Int. Cl.$^4$ ............................................. A61C 17/04
[52] U.S. Cl. ...................................................... 433/96
[58] Field of Search ....................... 433/91, 96; 128/136

[56]  References Cited
U.S. PATENT DOCUMENTS

| | | | |
|---|---|---|---|
| 2,731,722 | 1/1956 | Wilen | 32/28 |
| 3,090,122 | 5/1963 | Erickson | 32/33 |
| 3,139,088 | 6/1964 | Gallehers, Jr. | 128/208 |
| 3,460,255 | 8/1969 | Hutson | 32/33 |
| 4,434,036 | 1/1984 | Lokken | 433/116 |
| 4,611,992 | 9/1986 | Lokken | 433/116 |
| 4,776,793 | 10/1988 | La Rocca | 433/96 |

FOREIGN PATENT DOCUMENTS 67775  4/1955  France ................................. 433/91

Primary Examiner—Robert Peshock
Attorney, Agent, or Firm—J. Helen Slough

[57] ABSTRACT

A dental appliance for attachment to an aspirator operated by power vacuum means wherein the aspirator projecting into the mouth of a patient to evacuate fluid and debris therefrom is provided with a generally cup shaped double-walled receptacle providing a container to receive drippings of excess fluids or debris not caught by the tube portion projected into the mouth of the patient, power vacuum means associated therewith to provide passage of the same through openings in a lowermost wall of the container into tubular means associated therewith projecting upwardly of the receptacle and communicating with the vacuum means.

5 Claims, 2 Drawing Sheets

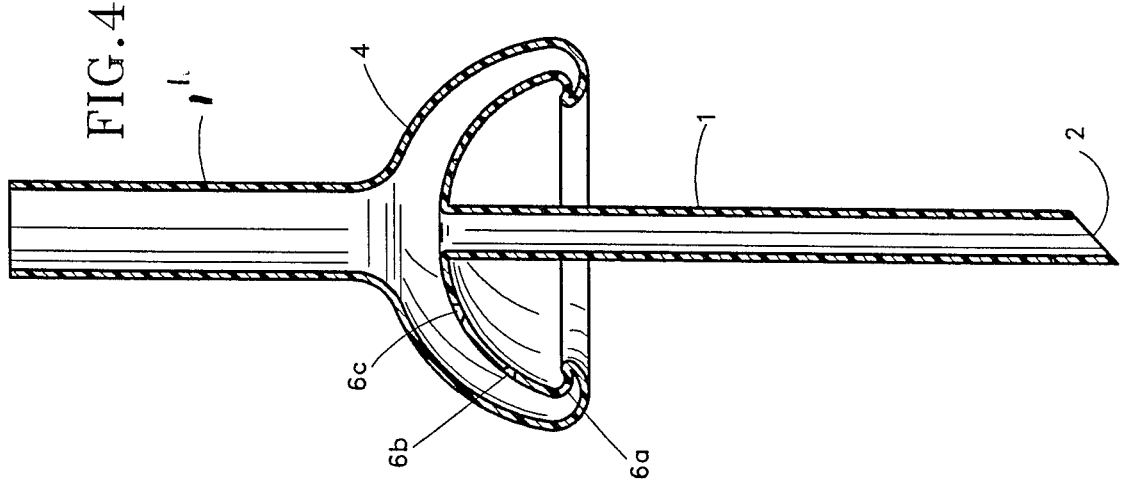
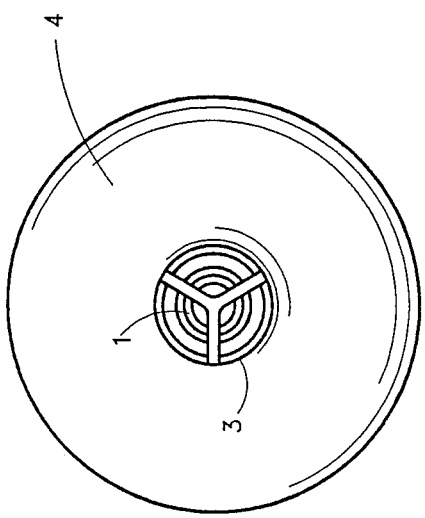
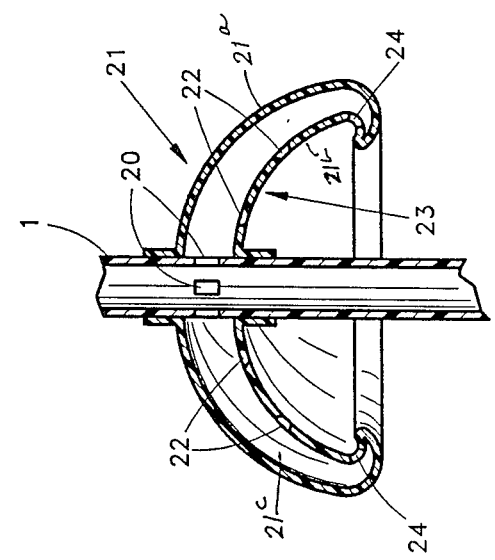
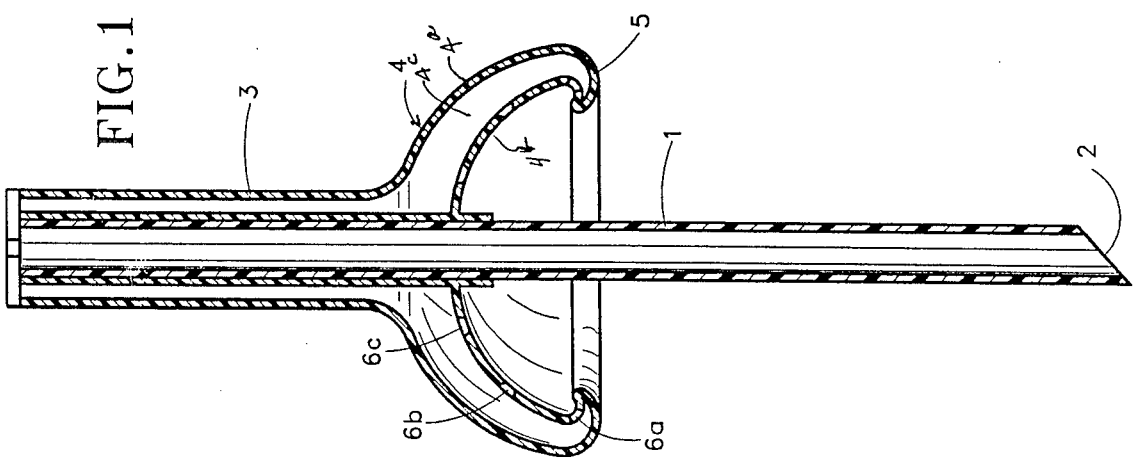

DENTAL ASPIRATOR

FIELD OF THE INVENTION

This invention relates to dental aspirators which are suction devices used to withdraw fluids and debris from the mouth of a patient during the course of dental work on said patient and particularly relates to power driven aspirators.

Improvements in such aspirators are described in my pending application Ser. No. 097,756, filed Sept. 17, 1987.

DESCRIPTION OF THE PRIOR ART

In the past, dental tools have been provided with guards, receptacles and anti-splash devices of the type shown in U.S. Pat. No. 2,731,732, wherein the guard is placed in the mouth and protects the depressed lining of the mouth or the tongue from engagement with a rotating grinding wheel; U.S. Pat. No. 4,424,036, which provides an inverted anti-splash cup spaced from water delivery means which is placed in the mouth of the patient, and which is transparent so that the dental prophylaxis treatment may be observed; U.S. Pat. No. 3,090,172, where the dental tool is an aspirator but the receptacle is also positioned in the patient's mouth; and U.S. Pat. No. 4,611,992 wherein the anti-splash means is placed over a tooth being treated for collection of debris and liquid from the mouth of the patient.

The present invention provides an anti-splash device similar to that of my prior application referred to above which provides a tip for a dental aspirator which is a suction device used to draw fluid and debris which accumulates due to the use of high powered tools, water sprays, cutting instruments, etc., from the mouth of the dental patient. The aspirator has a tube which projects into the mouth of the patient being treated, The aspirator is used to evacuate a patient's mouth during dental procedures of fluid and debris, for example saliva, blood, water and other debris and avoid splashing of the same. In the device of the present invention, the shield or skirt carried by the aspirator tube has a double walled contour, one wall of the shield and/or the aspirator tube provides a container formed by spacing of the walls which communicates through a tube projecting upwardly therefrom and with the source of the suction means and is provided with openings therein through which the fluid and debris are withdrawn by the suction means. The openings provided may be of various shapes, including funnel shapes, and the said shield may be formed integrally with the tube, be carried by a separate tube spaced from the aspirator tube surrounding the same or be secured as stated above to the aspirator tube, and derive its suction effect from power means associated therewith. Fluid or debris splashed outwardly from the mouth of the patient is thus redirected by the shield or skirt which captures the same within the container and is drawn off through the openings in the container by suction. During most dental procedures a water and air syringe is constantly in use, causing splashing of fluids and debris from the mouth. The power vacuum system employed to withdraw fluid by an aspirator causes the liquids and debris to be evacuated through the tube.

IN THE DRAWINGS

FIG. 1 is a sectional view of a first embodiment of my invention;

FIG. 2 is a top plan view of the embodiment of FIG. 1;

FIG. 3 is a sectional view of a second embodiment of the invention;

FIG. 4 is a sectional view of a third embodiment of the invention; and

Figure 5:
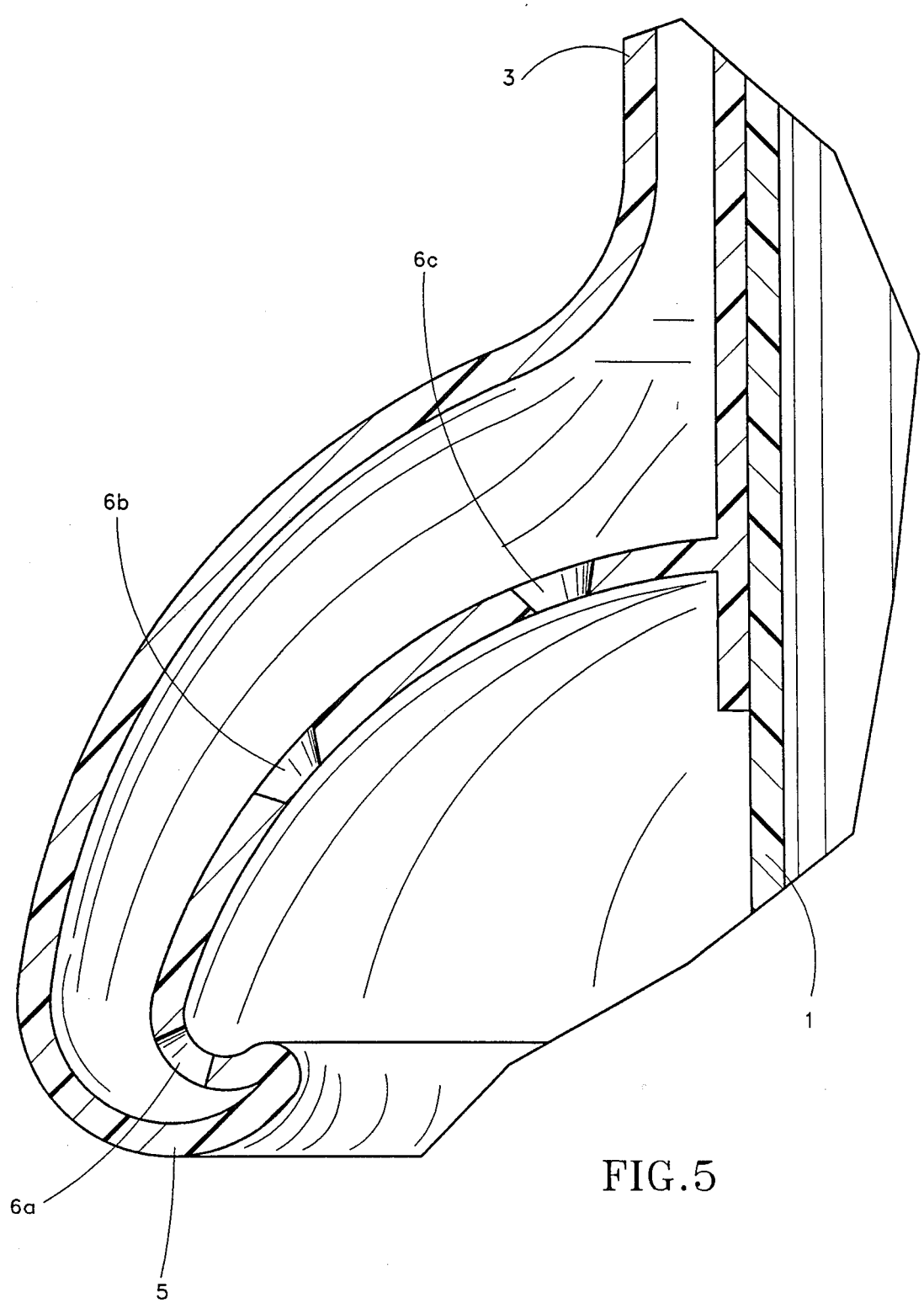
FIG. 5 is an elongated sectional view of a portion of the skirt and aspirator tube of the embodiment of FIG. 1.

Referring now to the drawings in which like parts are designated by like reference characters, in FIGS. 1 to 3 inclusive is shown a power driven dental tool known as an aspirator, which aspirator is used to draw fluids and debris from the mouth of a patient. The aspirator comprises an elongated flexible hollow tube 1 having a relatively more rigid tip portion 2 which normally is provided with slots (not shown) adjacent an end thereof, which tip extends into the mouth of the patient. The upper end of the tube of the aspirator is connected to a hose of a conventional aspirator or other vacuum source (not shown), drawing by suction, liquid and debris from the mouth of the patient. The said liquid and debris etc., accumulates therein due to the use of high powered tools, water sprays, cutting instruments, etc., by the dentist or dental assistant during treatment. A preferably cup shaped receptacle, shield or open cylinder 4 is secured to a tube 3 which, in the form of the invention shown in FIG. 1, is telescoped over the aspirator tube 1 and spaced therefrom, the shield 4 being of double-wall construction and terminates outwardly of the aspirator at its lower edge 5 preferably with inturned upwardly curved ends as shown. As shown in the embodiment of FIG. 4, the double-walled shield may be formed integrally with the aspirator flaring outwardly therefrom or secured thereto, as indicated in FIG. 3.

In FIGS. 1, 3 and 4, the receptacle, shield or cylinder 4 is shown as a double-walled inversely shaped cup provided with an uppermost wall 4a or 21a and a lowermost wall 4b or 21b, the walls providing, due to spacing provided between the uppermost and lowermost wall of said different forms of the invention, a container 4c within the said cup walls forming a basin for receiving fluid and debris splashed therein through openings 6 in the lowermost wall of the receptacle, which openings are designated in the drawings herein at 6a, 6b and 6c. The fluid and/or debris delivered to the containers 4c and 21c is drawn by suction therefrom by the power vacuum means through a tube associated therewith which in the form of FIG. 1 is the outer tube 3, the aspirator tube 1 in FIG. 3, and in the form of FIG. 4 is the aspirator tube 1'.

In the form of the invention of FIG. 3, openings 20 are provided in the aspirator tube 1 to provide egress by the suction means of the fluid or debris drawn into the container 21c through openings 22 in the shield and outwardly through openings 20 in the aspirator tube 1. The shield 21 is securely mounted on the aspirator tube as shown surrounding the same.

In all forms of the invention the openings in the lowermost wall of the shield as best shown in FIG. 5 are provided in the lowermost wall of the shield which, by virtue of suction from power vacuum means drawn through tubes 3 and/or tube 1 draws excess fluid and debris splashed or otherwise emitted from the mouth of the patient through the openings 6a, 6b, 6c through the tubes 1 in FIGS. 1, 3 and 5, the openings 22 in FIG. 3.

The receptacle may be of any material such as paper, celluloid, or the like. It should preferably be transparent to enable the dentist or his assistant to observe the same.

The receptacle may be of varied forms and, as for example shown in the figures herein, provided with inturned peripheral preferably curved ends about its lower periphery. It should be essentially of dome shape having a curved upper open umbrella or cup form disposed in such position on the aspirator tube or tube associated therewith. The openings therein enable excess fluid or debris to be carried into the aspirator tube or tube associated with the shield and said receptacle should be of a construction to collect fluid or debris passed through the openings and express the collected material from the same through egress means.

While I have described my invention in connection with preferred embodiments, it is to be understood that departures may be made therefrom without however departing from the spirit of my invention and the appended claims.

What I claim is:

1. A dental appliance for collecting and removing liquid and debris from the mouth of a patient during the conduct of dental operations therein comprising:

an aspirator adapted to be inserted into the mouth of the patient, said aspirator having an upwardly extending tube, power vacuum means adapted to withdraw said liquid and debris from the mouth and drawing the same outwardly through the tube, said aspirator being provided with double-walled inverted cup shaped receptacle disposed outwardly and securely mounted on said aspirator, spacing between the walls forming a container therebetween, openings in a lowermost wall of said container adapted to receive excess fluid and debris from the mouth drawing the sam through the said openings by suction created by said power vacuum means and expressing the same.

2. A dental appliance according to claim 1 wherein the aspirator tube projecting outwardly of the mouth is adapted to have the receptacle securely mounted thereon, the receptacle circumferentially surrounding the said tube and said tube is provided with other openings communicating with the container through which other openings the excess fluid and debris drawn by suction from the vacuum means is adapted to pass into the aspirator tube.

3. A dental appliance according to claim 1 wherein the receptacle is provided with an upwardly extending tube spaced from and surrounding the aspirator tube through which the excess fluid and debris in the container is drawn by suction.

4. A dental appliance according to claim 1 wherein the receptacle is integrally formed with and about a mid-section of the aspirator tube.

5. A dental appliance for collecting and removing liquid and debris from the mouth of a patient during the conduct of dental operations therein comprising:

an aspirator adapted to be inserted into the mouth of the patient, said aspirator having an upwardly extending tube, a second tube spaced from and surrounding the aspirator tube, power vacuum means adapted to withdraw said liquid and debris from the mouth and drawing the same outwardly through the aspirator tube; an inverted receptacle securely mounted on the said second tube, said second tube drawing excess fluid captured by the receptacle from the same.

* * * * *